Figure 1:
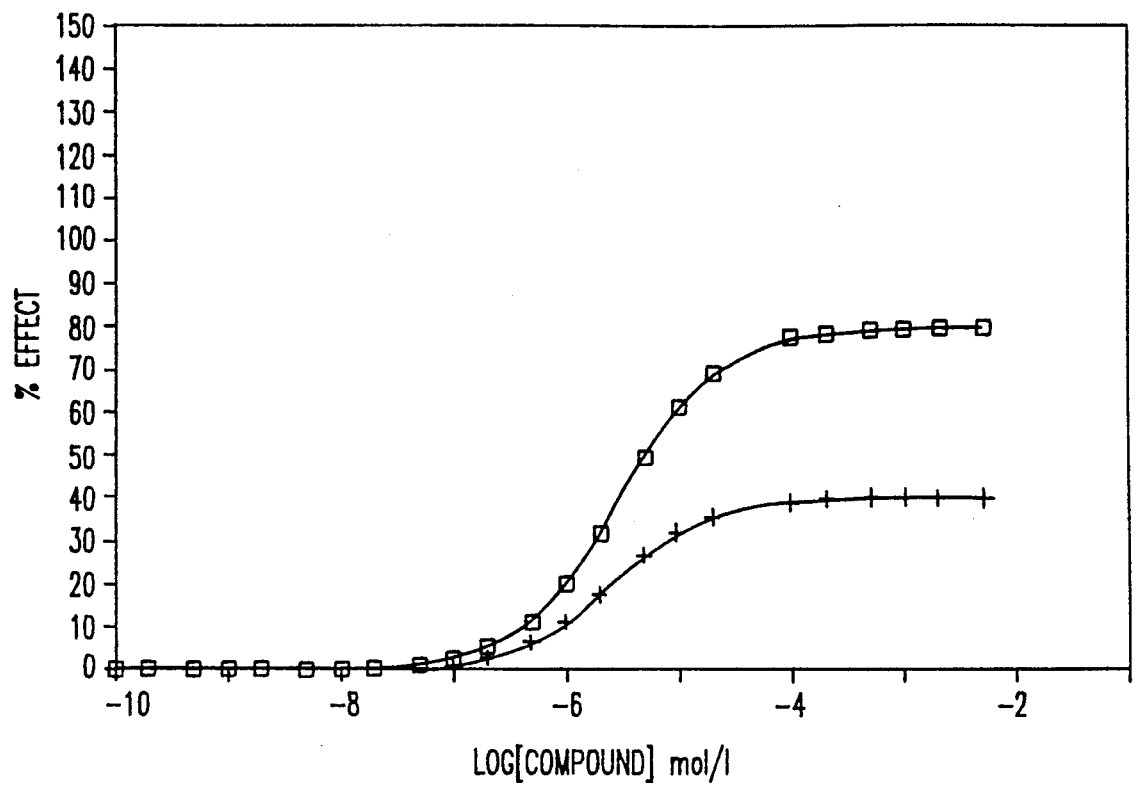

United States Patent [19]

Van Dasler et al.

[11] Patent Number: 5,266,589

[45] Date of Patent: Nov. 30, 1993

[54] METHOD OF INCREASING THE MUSCLE/FAT RATIO IN AGRICULTURAL DOMESTIC ANIMALS

[75] Inventors: Johan K. Van Dasler; Jan Van Dijk, both of Weesp, Netherlands

[73] Assignee: Duphar International Research B.V., Weesp, Netherlands

[21] Appl. No.: 795,386

[22] Filed: Nov. 21, 1991

[30] Foreign Application Priority Data

Nov. 26, 1990 [NL] Netherlands ................. 9002565

[51] Int. Cl.$^5$ ................ A61K 31/38; A61K 31/18; A61K 31/135
[52] U.S. Cl. ................ 514/438; 514/604; 514/653
[58] Field of Search ................ 514/653, 654, 438, 604

[56] References Cited

U.S. PATENT DOCUMENTS

| | | | |
|---|---|---|---|
| 4,407,819 | 10/1983 | Kiernan et al. | 514/653 |
| 4,761,421 | 8/1988 | Muir | 514/653 |
| 4,873,240 | 10/1989 | Arch | 514/231.5 |
| 4,880,834 | 11/1989 | Arch | 514/567 |
| 5,047,434 | 9/1991 | Simon et al. | 514/653 |

FOREIGN PATENT DOCUMENTS 0103830 3/1984 European Pat. Off. .
0308157 3/1989 European Pat. Off. .

OTHER PUBLICATIONS

Commonwealth Agricultural Bureaux, ON060-00458, Nutritition ABS and REV/SER B; F. Locniskar et al.: "The Effect of Beta-. . . " Comparative Biochemistry and Physiology, vol. 77C, No. 1, 1984 pp. 39-42.
American Journal of Physiology: Endocrinology and Metabolism, vol. 15, No. 1, Jan. 1987, pp. E85-E95, Mersmann: "Acute Meta . . . ".
H. J. Mersmann: "Specificity of Beta-Adrenergic . . . " American Journal of Physiology: Endocrinology and Metabolism, vol. 15, No. 1, Jan. 1987, pp. E85-E95, Mersmann: Acute Meta . . . .

*Primary Examiner*—Frederick E. Waddell
*Assistant Examiner*—K. Weddington
*Attorney, Agent, or Firm*—Stevens, Davis, Miller & Mosher

[57] ABSTRACT

The invention relates to a method of improving the growth and the feed efficiency and of increasing the muscle/fat ratio of agricultural domestic animals, in particular bovine animals and sheep, by administering to the animals a composition which comprises as an active substance a compound of the general formula

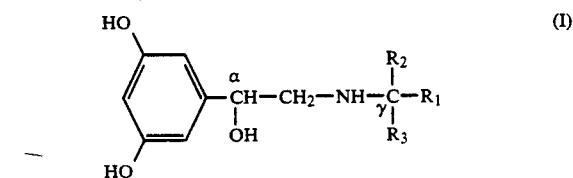

(I)

wherein:
$R_1$ is a phenylalkyl group the alkyl group of which comprises 1-3 carbon atoms and the phenyl group of which may be substituted with one or more substituents selected from the group consisting of hydroxy, methoxy, fluoro and methylsulphonylamino, or wherein $R_1$ is a thienyl alkyl group or a tetrahydrofurylalkyl group the alkyl group of which comprises 1-3 carbon atoms; or wherein $R_1$ is an optionally branched alkyl group having 1-8 carbon atoms which optionally is substituted with a $C_1$-$C_4$ alkoxy group, a hydroxy group, a $C_1$-$C_4$ alkoxycarbonyl group or a carboxy group; and wherein $R_2$ and $R_3$ are each independently methyl or ethyl; or an acid addition salt of the said compound.

The invention further relates to a composition, in particular intended as a feed additive, which comprises such a phenylalkylamino derivative as an active substance.

3 Claims, 2 Drawing Sheets

METHOD OF INCREASING THE MUSCLE/FAT RATIO IN AGRICULTURAL DOMESTIC ANIMALS

The invention relates to a method of increasing the muscle/fat ratio and improving the growth and the feed efficiency of agricultural domestic animals, selected from ruminants and poultry, by administering to the said animals a phenyl alkylamino derivative in a quantity which is effective for this purpose. The invention further relates to a composition, in particular intended as an animal feed additive, which comprises such a phenyl alkylamino derivative as an active substance.

Compounds for the above application, also termed repartitioning agents, have attracted increasing interest in the past few years. It has been found that phenyl alkylamino derivatives, of which an activity as beta-adrenergic agonists is known, are suitable in particular for this purpose. Phenyl alkylamino derivatives with the above application are known, for example, from the following patent publications: the U.S. Pat. Nos. 4,407,819 and 4,690,951, the British Patent Specification 2,117,600 and the published European Patent Applications 26,298, 103,830, 154,923, 224,001, 253,258 and 259,750.

Agricultural domestic animals as defined above are to be understood to include notably bovine animals, sheep, pigs and poultry.

A phenyl alkylamino derivative, described in U.S. Pat. No. 4,690,951 and in British Patent Specification 2,117,600, has meanwhile been recommended for this purpose under the name of Ractopamine ®. However, this compound, as well as the commercially available Clenbuterol ®, shows serious side effects because in the dosages required for the intended purpose an undesired influence on the heart is exerted. Such an activity is considered as a serious disadvantage. As a matter of fact, in the intended use in livestock the active substance to be used as a repartitioning agent must be administered continuously for a considerable period of time at the end of the growth period of the animals. This means a constant burden on the heart, which has an unfavorable influence on the well-feeling and hence on the physical development of the animals, and also constitutes a risk factor for the said animals.

An excellent indication for the activity as a repartitioning agent, i.e. for the activity to increase the muscle/fat ratio of agricultural domestic animals, is the lipolytic activity, i.e. the conversion of triglycerides into glycerol and fatty acids in the adipocytes. It is the object of the present invention to increase the muscle/fat ratio in agricultural domestic animals by using a phenyl alkylamino derivative which on the one hand has a high lipolytic activity, but on the other hand does not exhibit the above-mentioned drawback.

According to the present invention this object can be achieved by using a compound of the general formula

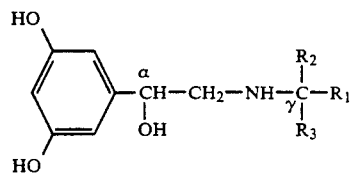

wherein:

$R_1$ is a phenylalkyl group the alkyl group of which comprises 1-3 carbon atoms and the phenyl group of which may be substituted with one or more substituents selected from the group consisting of hydroxy, methoxy, fluoro and methylsulphonylamino; or wherein $R_1$ is a thienylalkyl group or a tetrahydrofurylalkyl group the alkyl group of which comprises 1-3 carbon atoms; or wherein $R_1$ is an optionally branched alkyl group having 1-8 carbon atoms which optionally is substituted with a $C_1$-$C_4$ alkoxy group, a hydroxy group, a $C_1$-$C_4$ alkoxycarbonyl group or a carboxy group; and wherein $R_2$ and $R_3$ are each independently methyl or ethyl; or an acid addition salt of the said compound.

As will become apparent from the specific examples, the compounds mentioned hereinbefore do not show any detrimental activity on the heart in those concentrations which promote the lipolysis in various agricultural domestic animals, for example, bovine animals and sheep. As a result of this the compounds mentioned hereinbefore may be used without any side effects for the intended purpose, namely improving the growth and the feed efficiency of agricultural domestic animals. This in contrast with Ractopamine ® mentioned hereinbefore which shows a considerable heart activity in the required concentration. The favorable activity of the compounds according to the invention is related to the chemical structure of the said compounds, namely a 3,5-dihydroxyphenyl substituent at the α-C atom in combination with a tertiary C-atom in the γ-position. In European Patent Application 103,830 mentioned hereinbefore a 3,5-dihydroxyphenyl alkylamino derivative, namely 1-(3,5-dihydroxyphenyl)-2-(3-phenylpropylamino)propanol, is recommended for this purpose. For comparison, Fenoterol ®, likewise a 3,5-dihydroxyphenyl alkylamino derivative and a known beta-adrenergic agonist, has also been tested. It will become apparent from the specific examples that the said compound has the same disadvantages as Ractopamine ® and Clenbuterol ® mentioned hereinbefore, namely that it shows a considerable heart activity in the concentration required for the intended purpose.

A compound of the general formula

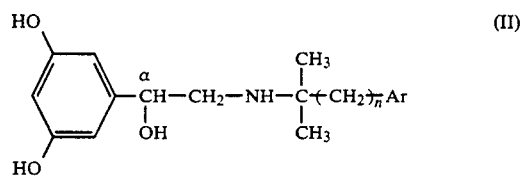

wherein:

n is 1, 2 or 3, and

Ar is a thienyl group or a phenyl group which may be substituted with hydroxy, methoxy, fluoro or methylsulphonylamino, or an acid addition salt of the said compound, has been fond to be particularly suitable for the application mentioned hereinbefore.

Phenylalkylamino derivatives having an activity as beta-adrenergic agonists usually have one or more asymmetrical carbon atoms (chiral centers) and may hence occur in several steric configurations. This has been signalled already by Van Dijk and coworkers who in 1965 devoted a paper to these compounds and their interesting pharmacological properties; Receuil Trav. Chim. Pays Bas 84 (1985), pp. 521-539. Anderson and coworkers have investigated whether the effectiveness of phenylalkylamino derivatives in the above application in livestock also depends on the selected mixing ratio of optical isomers. They conclude from the experiments performed by them that the improvement of the growth of the animals can be obtained with any desired mixture of optical isomers: U.S. Pat. No. 4,690,951, column 16, lines 26-30. In the light of this statement made by Anderson and coworkers it is surprising that it has been found that the desired activity may be ascribed in particular to compounds as defined hereinbefore which have the R configuration at the α-C-atom. Therefore, compounds according to the general formula I or II shown hereinbefore may be used successfully for the intended purpose in particular in case they have the R configuration at the α-C-atom.

An example of a compound which has proved to be pre-eminently suitable for the intended purpose is 1-(3,5-dihydroxyphenyl)-2-[1,1-dimethyl-2-(4-hydroxyphenyl)ethylamino]ethanol, as well as acid addition salts of this compound.

The last-mentioned compound is known in literature. Mersmann has investigated the lipolytic activity of this compound in comparison with other phenylalkylamino derivatives, for example Fenoterol ®, in vitro, i.e. in adipose tissue of pigs, and in the pigs themselves, so in vivo: Comp. Biochem. Physiol. 77C (No. 1), 1984, 39-42; Am. J. Physiol. 252 (1, Pt. 1), 1987, E85-E95. It appears from these publications that a low lipolytic activity is found for the compound in question. The relative $ED_{50}$ is approximately ten times as high as that of Fenoterol ®; this means that an approximately ten times as high concentration is necessary to reach the same lipolytic activity in swine adipose tissue as with Fenoterol ®. Such results are not stimulating for further examination into this compound. It is therefore surprising—as will become apparent from the specific examples—that 1-(3,5-dihydroxyphenyl)-2-[1,1-dimethyl-2-(4-hydroxyphenyl)-ethylamino]ethanol combines a remarkably high lipolytic activity on bovine and ovine adipocytes with a low heart effect. As a result of this it is possible to use this compound as well as chemically related phenylalkylamino derivatives according to the present invention as so-called repartitioning agents for agricultural domestic animals, in particular for bovine animals and sheep. In fact, detrimental heart activity is not found in the concentration required for the intended use, as will become apparent from the specific examples. Exactly a wide range of application, including also the use in bovine animals and sheep, is of great practical importance.

For the same above application terbutaline is recommended. According to Mersmann (see above) however, terbutaline is even less suitable for the intended use than Fenoterol ®, because terbutaline appeared to be less active in lipolysis and more active in increasing heart rate.

Examples of acid addition salts are addition salts of the above compounds with various acids, for example, hydrochloric acid, hydrobromic acid, sulphuric acid, phosphoric acid, nitric acid, or organic acids, such as citric acid, fumaric acid, tartaric acid, acetic acid, maleic acid, benzoic acid, p-toluenesulphonic acid, methanesulphonic acid, and the like.

In order to facilitate the administration, the compound is brought into a form suitable for this purpose. The invention therefore also relates to a composition which is suitable for administration to warm-blooded animals and which comprises a compound as defined hereinbefore as an active substance. For parenteral administration the compound is brought into a form suitable for injection, for example, as an acid addition salt dissolved in a liquid which consists substantially of water, for example, a physiological saline solution or a dilute glucose solution. However, the compound is preferably administered orally and is then formulated to a composition suitable for this purpose, preferably a feed additive.

The stereoisomeric compound optionally to be used may be separated from the other stereoisomers by means of techniques known per se, for example, selective crystallisation of an addition salt with a stereoisomer of an acid with a chiral center. However, a stereochemically pure starting substance or a stereochemically pure intermediate product obtained by isomer separation is preferably used. This substance may then be converted in one or more reaction steps into the desired stereochemically pure compound, for example, as described in the paper by Van Dijk and coworkers mentioned hereinbefore.

It is known, for example, from a contribution by R. G. Vernon in "New perspectives in Adipose Tissue; structure, function and development", page 76, edited by Cryer and Van, Butterworths 1984, London, that there exists a good relationship between the lipolytic activity on the one hand and the activity as a repartitioning agent on the other hand. This means that a high value for the lipolytic activity is predictable for the increase of the muscle/fat ratio and for improving the growth and the feed efficiency of agricultural domestic animals. The influence of the tested compounds on the lipolysis of adipocytes is described in example I hereinafter. Bovine and ovine adipocytes, i.e. adipocytes of representative examples of agricultural domestic animals, have been used in this example.

The heart activity has been determined in heart tissue of rats. It is known that rats are just as suitable for the determination of the heart activity (chronotropy) as the agricultural domestic animals mentioned hereinbefore.

The invention will now be described in greater detail with reference to the following specific examples.

EXAMPLE I

Lipolytic Activity

Pieces of adipose tissue of approximately 600×600 μm, isolated from bovine animals or sheep, are provided in a teflon container containing: 3 ml of Krebs-Henseleit buffer having a pH of 7.4, 1% w/v of demineralized bovine serum albumin (BSA), 0.33 mg/ml of collagenase and 200 nM of adenosine. The adipocytes are isolated by shaking the container at 37° C. under carbogen gassing (approximately 5% $CO_2$ in 95% $O_2$). After 1 hour the suspension is filtered through nylon gauze (100 μm) and washed 2 times with Krebs-Henseleit buffer at room temperature. The incubations are carried out in duplicate, each incubation mixture consisting of 50 μl of the filtered cell suspension, 100 μl of the compound to be tested, 2% w/v of BSA and 50 μg/ml of $Na_2S_2O_5$ (antioxidant) in 2.85 ml of Krebs-Henseleit buffer. Incubation: 90 minutes at 37° C. while shaking and gassing with carbogen. After the incubation, extraction is carried out with 3 ml of 2-propanol/n-hexane/1N-$H_2SO_4$ (40:20:1) mixture. In the organic layer the produced free fatty acids (FFA) are determined. This determination is carried out as follows: 150 μl of sample are diluted with 1 ml of chloroform and then mixed with copper reagent (10% $Cu(NO_3)_2$/2M triethanolamine/2N acetic acid=10:9:1); 0.2% w/v of sodium diethyldithiocarbamate is added. The yellow color is measured in a colorimeter and is a measure of the FFA-production. From the obtained results dose response curves are made from which the $pEC_{50}$ value in comparison with the blank is derived per tested compound. The $pEC_{50}$ value, which is the negative logarithm of the reagent concentration at which 50% of the maximum effect is reached, is a measure of the lipolytic activity. The determinations have been carried out in relation to a known compound having an activity as a beta-adrenergic agonist, namely Isoprenaline ® or Isoproterenol ® [1-(3,4-dihydroxyphenyl)-2-(isopropylamino)ethanol]. In addition to the fond $pEC_{50}$ values, the values for the intrinsic activity ("i.a.") have been recorded in Table A hereinafter. The intrinsic activity is the maximally achievable activity, also measured again with respect to Isoprenaline ®.

TABLE A

| | Lipolytic activity: $pEC_{50}$ and i.a. | | | |
|---|---|---|---|---|
| | Bovine | | Ovine | |
| Tested compound | $pEC_{50}$ | i.a. | $pEC_{50}$ | i.a. |
| (1) | 5.5 | 0.8 | 6.3 | 1.4 |
| Ractopamine ® | 5.6 | 0.6 | | |
| Fenoterol ® | 6.1 | 0.8 | | |
| Clenbuterol ® | 5.8 | 0.3 | | |

(1) = 1-(3,5-dihydroxyphenyl)-2-[1,1-dimethyl-2-(4-hydroxyphenyl)ethylamino]ethanol.

It appears from the above results that the intrinsic lipolytic activity of compound (1) which according to the invention may be used as a repartitioning agent, in particular for bovine animals and sheep, is significantly higher than that of the phenylalkylamino derivatives Ractopamine ® and Clenbuterol ®, which were also tested.

EXAMPLE II

Heart Activity

Tissues from male Wistar rats are placed, immediately after isolation, in Krebs solution of the following composition (mM): NaCl 117.5; KCl 5.6; $MgSO_4$ 1.18; $CaCl_2$ 2.5; $NaH_2PO_4$ 1.28; $NaHCO_3$ 35.0; glucose 5.5; pH 7.4 at 37° C. under an atmosphere of 95% $O_2$ and 5% $CO_2$. The substances are tested with respect to their chronotropic effect on isolated right atria under a preload with 0.5 g, in an organ bath which contains the above Krebs buffer solution and is kept at 37° C. Dose-response curves with Isoprenaline ® are determined. The results are again expressed as $pEC_{50}$ values and, in relation to Isoprenaline ®, as intrinsic activities ("i.a."). The results are recorded in Table B below.

TABLE B

| Chronotropic effect on the right atrium. | | |
|---|---|---|
| Tested compound | $pEC_{50}$ | i.a. |
| (1) | 5.6 | 0.4 |
| Ractopamine ® | 7.5 | 1.0 |
| Fenoterol ® | 6.6 | 1.0 |
| Clenbuterol ® | 7.3 | 0.4 |

It appears from the above results that the heart activity of active substance (1) is considerably lower than that of the substances Ractopamine ®, Fenoterol ® and Clenbuterol ®, which were also tested.

EXAMPLE III

Dose-Response Curves Lipolytic Effect and Heart Activity

Figure 2:
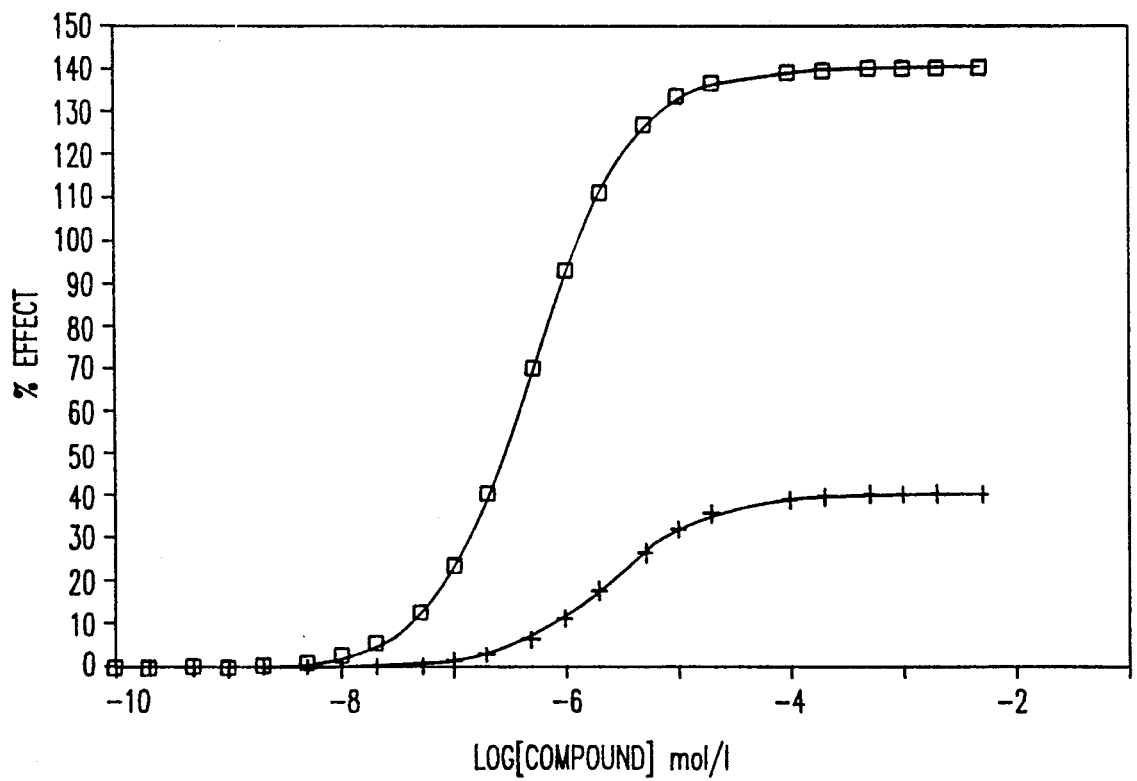
Figure 3:
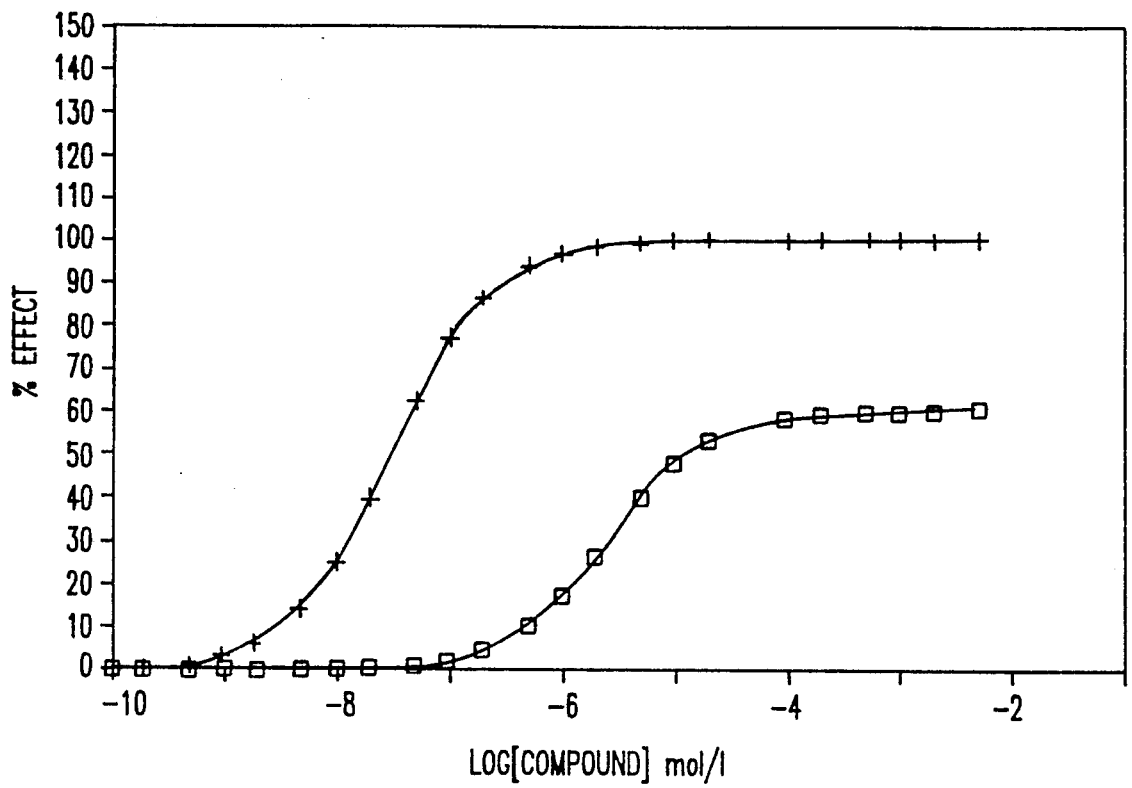
Figure 4:
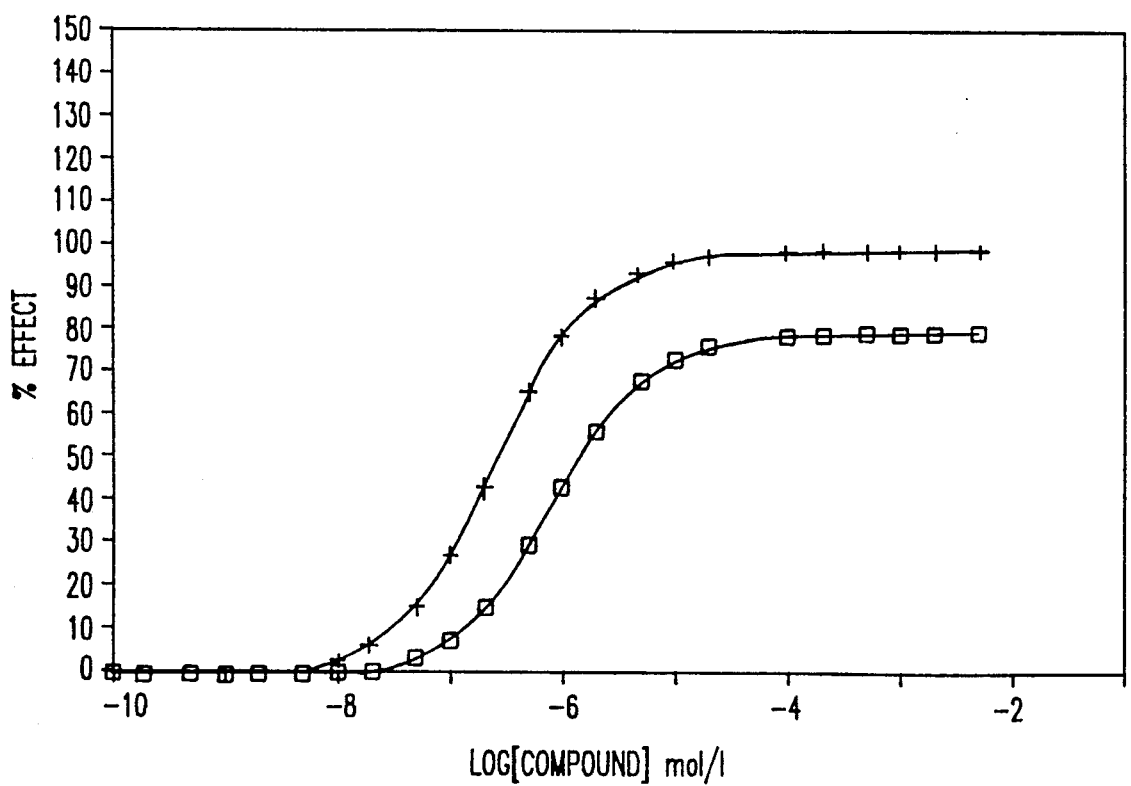

The dose response curves are recorded in the accompanying FIGS. 1, 2, 3 and 4, the log. of the concentration of the tested compound in mol/l is plotted on the X-axis, the "% effect", which is the measured effect in comparison with the equally tested Isoprenaline ® in %, is plotted on the Y-axis; □=lipolysis; +=chronotropy. FIG. 1 shows the lipolytic activity on bovine adipocytes and the heart activity when using the above-mentioned compound (1), FIG. 2 shows the lipolytic activity on ovine adipocytes and the heart activity when using the same compound. FIG. 3 shows the lipolytic activity on bovine adipocytes and the heart activity when using Fenoterol ®, and FIG. 4 shows those when using Ractopamine ®. It will be clear from the curves that the use of the known substances is always associated with a serious increase of the heart activity (chronotropy), while the compound (1) to be used according to the invention can be effectively used for the intended purpose without a burdensome heart activity being experienced.

We claim:

1. A method of improving the growth and the feed efficiency and of increasing the muscle/fat ratio of agricultural domestic animals selected from ruminants and poultry, by administering to the animals a composition which comprises a phenylalkylamino derivative in a quantity sufficient for improving the growth and the feed efficiency of agricultural domestic animals, characterized in that the active substance is a compound of the formula

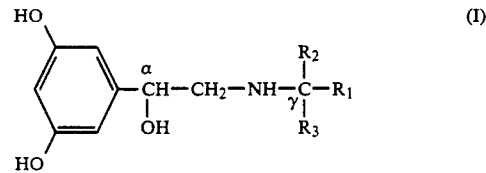

wherein:
R₁ is a phenylalkyl group, the alkyl group of which comprises 1-3 carbon atoms and the phenyl group of which may be substituted with hydroxy, methoxy, fluoro and methylsulphonylamino, or wherein R₁ is a thienyl alkyl group, the alkyl group of which comprises 1-3 carbon atoms; and wherein R₂ and R₃ are each methyl; or an acid addition salt of said compound and a carrier.

2. A method as claimed in claim 1, characterized in that the phenylalkylamino derivative or acid addition salt thereof has the R configuration at the α-C atom.

3. A method as defined in claim 1, wherein the domestic animals are selected from bovine animals and sheep.

* * * * *